United States Patent [19]

Lormeau et al.

[11] Patent Number: 4,686,288

[45] Date of Patent: Aug. 11, 1987

[54] PROCESS FOR PREPARING MUCOPOLYSACCHARIDE COMPOSITIONS HAVING HIGH ANTITHROMBOTIC ACTIVITY, THE COMPOSITIONS OBTAINED AND THEIR USE AS MEDICAMENTS

[75] Inventors: Jean-Claude Lormeau, Maromme; Jean Choay, Paris, both of France

[73] Assignee: D.R.O.P.I.C., Paris, France

[21] Appl. No.: 681,017

[22] Filed: Dec. 13, 1984

Related U.S. Application Data

[63] Continuation-in-part of Ser. No. 323,567, Mar. 20, 1981, Pat. No. 4,500,519, which is a continuation-in-part of Ser. No. 204,505, Nov. 6, 1980, abandoned, which is a continuation of Ser. No. 91,164, Nov. 5, 1979, abandoned.

[30] Foreign Application Priority Data

Mar. 20, 1980 [FR] France ............................. 80 06282

[51] Int. Cl.⁴ .......................... C07H 1/00; C08B 37/10
[52] U.S. Cl. ..................................... 536/21; 536/123; 536/124
[58] Field of Search ......................... 536/21, 124, 123; 514/56

[56] References Cited

U.S. PATENT DOCUMENTS

| | | | |
|---|---|---|---|
| 4,175,182 | 11/1979 | Schmer | 536/21 |
| 4,281,108 | 7/1981 | Fussi | 536/21 |
| 4,474,770 | 10/1984 | Lormeau et al. | 536/21 |
| 4,486,420 | 12/1984 | Lormeau et al. | 536/21 |
| 4,496,550 | 1/1985 | Lindahl et al. | 536/21 |
| 4,500,519 | 2/1985 | Lormeau et al. | 536/21 |

FOREIGN PATENT DOCUMENTS

| | | | |
|---|---|---|---|
| 2002406 | 2/1979 | United Kingdom | 536/21 |
| 2071127 | 9/1981 | United Kingdom | 536/21 |

Primary Examiner—Johnnie R. Brown
Attorney, Agent, or Firm—Weiser & Stapler

[57] ABSTRACT

The invention relates to a process for preparing mucopolysaccharides having high anti-thrombotic activity compared to heparin. The mucopolysaccharides are obtained from a mucopolysaccharide composition having high anti-thrombotic activity and a ratio of YW-/USP Titer higher than that of heparin by fractionation to remove, selectively, the mucopolysaccharide chains having less than six saccharide units.

17 Claims, 4 Drawing Figures

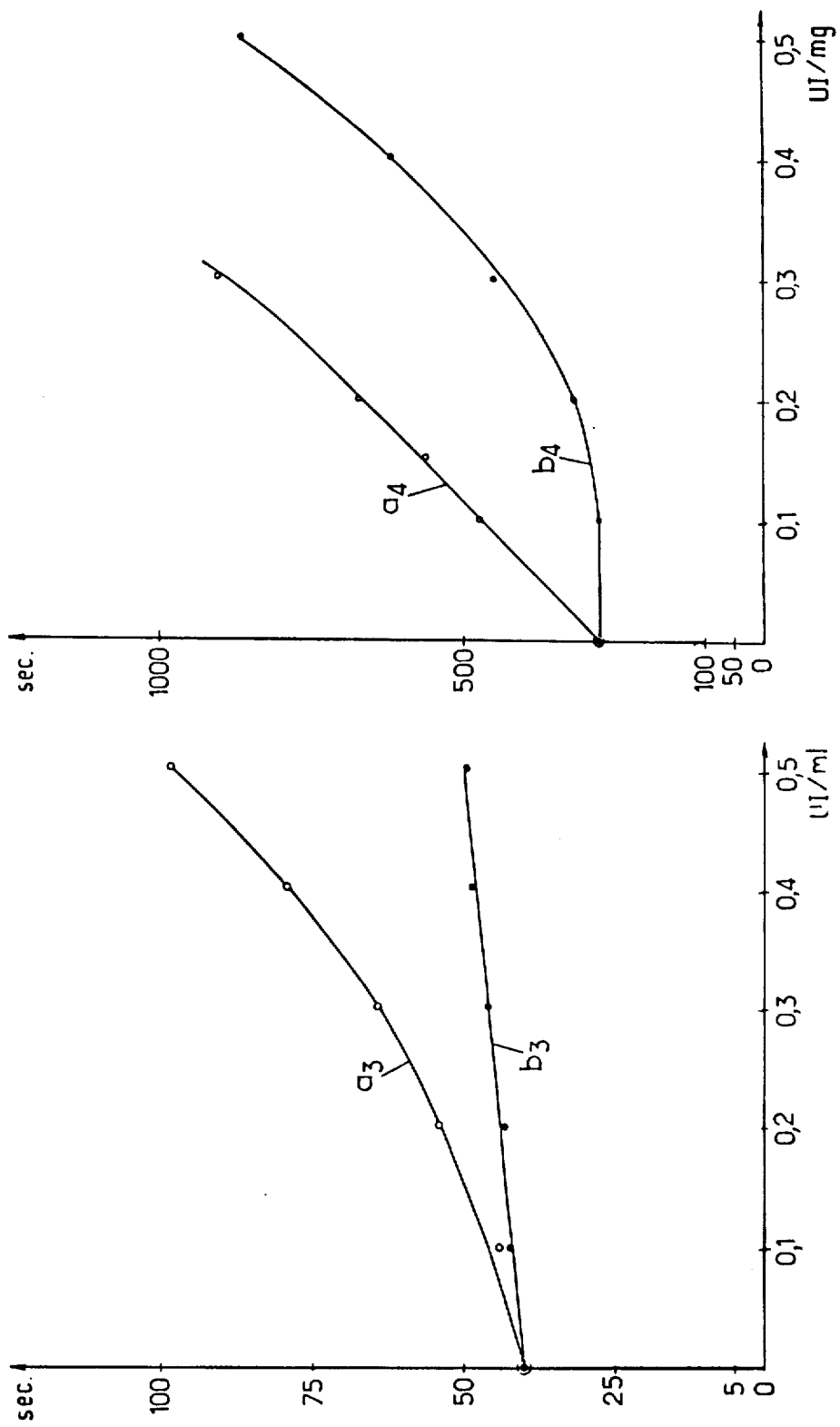

PROCESS FOR PREPARING MUCOPOLYSACCHARIDE COMPOSITIONS HAVING HIGH ANTITHROMBOTIC ACTIVITY, THE COMPOSITIONS OBTAINED AND THEIR USE AS MEDICAMENTS

This is a continuation-in-part of pending U.S. application Ser. No. 323,567, filed Mar. 20, 1981, now U.S. Pat. No. 4,500,519, which is a continuation-in-part of U.S. application Ser. No. 204,505, filed Nov. 6, 1980, now abandoned, which is a continuation of U.S. application Ser. No. 091,164, filed Nov. 5, 1979, now abandoned.

BACKGROUND OF THE INVENTION

The invention relates to a process for preparing mucopolysaccharide compositions endowed with high antithrombotic activity, the compositions obtained and their use as an active principle of a medicament.

It is known that compositions of this type have been obtained from heparin by alcoholic extraction, or again, by depolymerisation by chemical or enzymatical route.

In general, these processes enable the production of compositions or fractions consisting of mucopolysaccharides or MPS whose chains contain about 25 to 30 units at the most and possess an anti-Xa activity measured by the Yin Wessler titer (YW) higher than that of heparin and an overall anticoagulant activity, expressed by the USP titer, less than that of heparin, this titer can even have a value which is very low to practically nil.

These products have the interest of exerting a more specific activity than heparin on certain steps brought into play in the coagulation process.

According to the operational conditions used for their production, these products have YW/USP ratios and values of the YW titers within a given range, which permits the products to be selected which appear most appropriate for a given treatment.

The production of these products easily is naturally of essential interest.

In the research for means enabling the easy production of compositions corresponding to a given profile as regards, in particular, their YW titer and their ratio of YW to USP titers, Applicants have observed that by operating under particular conditions, it is possible to isolate such products from other MPS compositions.

These studies have, in addition, resulted in developing a new family of MPS possessing biological activities of great interest.

It is therefore an object of the invention to provide a novel process for preparing compositions of MPS with high antithrombotic activity whose simple employment enables products of great usefulness to be made easily available.

It relates also to providing MPS compositions possessing particularly a biological activity in the field of coagulation.

It is another object of the invention to provide medicaments endowed with high antithrombotic activity, used for the prevention and/or treatment of thromboses.

GENERAL DESCRIPTION OF THE INVENTION

According to the invention there is provided a process characterized in that compositions formed from a majority of MPS chains endowed with high antithrombotic activity and possessing a ratio of YW/USP titer higher than that of heparin are subjected to at least one fractionation step, in order to separate selectively those of the MPS chains which possess less than about 6 units. These chains show a ratio of YW to USP titer smaller than those of the starting compositions but higher than those of heparin.

Preferably, the fractionation step is carried out by means of a mixture of water containing an inorganic salt and organic solvent, this solvent being selected from among those in which at least a majority of the products sought is selectively insoluble.

The relative proportions of inorganic salt and of solvent are adjusted and this according to the pH of the medium to obtain the desired precipitation.

According to a preferred feature of the invention, the organic solvent is advantageously an alcoholic solvent, more especially ethanol.

According to another preferred feature, the organic salt used is constituted, particularly, by the sodium or potassium chloride or any other salt miscible in the organic solvent used.

According to another preferred feature, the pH of the reaction mixture is adjusted to a value corresponding to an acid pH, more especially to a pH less than 4.

According to a preferred embodiment of the invention, the MPS compositions employed for the fractionation possess a ratio of the YW to USP titers of at least about 10 and a Yw titer of about 200 to 250 u/mg.

The fractionation is carried out by means of an organic solvent enabling the selective precipitation of the MPS possessing the highest molecular weights and, consequently, a ratio of the YW to USP titers less than 10, particularly than 6, preferably than 5, and more especially in the vicinity of 4.

Preferably, the organic solvent is an alcoholic solvent, more especially ethanol.

The employment of the features which follow enables the production satisfactorily more especially of MPS possessing a ratio of the YW to USP titers below 10, preferably of about 6 to 3, more especially of the order of 4 and a YW titer higher than that of heparin and at least about 180 to 200 u/mg.

The MPS compositions corresponding to the characteristics of YW and USP titers given above are placed in solution in a proportion of 5% w/v in water containing 10 g/l of NaCl.

After adjustment of the pH to 3.8, the fractionation of these MPS is carried out by means of one volume of ethanol. The precipitate formed which contains the desired products is then recovered.

Preferably, the MPS compositions employed possess at the reducing end, a unit of 2,5 anhydromanno structure, preferably selected from among 2,5-anhydromannose, 2,5-anhydromannitol or 2,5-anhydromannonic acid groups.

These compositions are advantageously obtained by a partial depolymerisation process of heparin under the action of chemical agents such as nitrous acid. Recourse is had particularly to the process described by Applicants in the second application for a certificate of addition n° 80 06282 of 20.03.1980 to patent FR No. 78 31357 of 6.11.1978 or again to a depolymerisation process of this type, based on self-regulation of the depolymerisation reaction.

A process of this kind is described in patent application FR No. 81 07283 of 10.04.1981 in the name of Applicants.

The MPS compositions recovered on precipitation are characterised in that they are essentially formed of chains (1) of an average molecular weight of 3000 to 6000 daltons, particularly from 4000 to 5000, (2) possessing a YW titer of about at least 180 to 200 u/mg and a ratio of the YW/USP titer, less than 10, particularly of about 6 to 3,(3) terminated by units of 2.5-anhydromanno structure.

These compositions are endowed with biological activities enabling them in particular to control specifically certain steps of blood clotting.

Their high biological activity enables them to be used at low doses which renders them particularly suitable for the prevention of thromboses.

The study of these products shows that they are capable of exerting a powerful antithrombotic activity. In addition, derivatives according to the invention have great interest for combating disorders of the vascular wall, (atherosclerosis and arterosclerosis) and aging of the tissues.

In addition, they have the advantage of not having an effect of activation on platelet aggregation and not resulting in thrombocytopenia. They also have the advantage of being practically devoid of effect on bleeding time, which removes risks of hemorrhage. These two properties are extremely important for medical applications.

In addition, there is observed particularly subcutaneously a prolonged pharmacokinetics, which also gives great interest to these products.

The compositions of the invention are, moreover, advantageously devoid of toxicity.

These products are hence particularly valuable for developing medicaments usable, particularly, for the prevention of treatment of thrombosis and aging of the tissues.

The invention hence relates also to pharmaceutical preparations which contain an effective amount of these compositions in association with pharmaceutical excipients and more especially pharmaceutical preparations devoid of pyrogenic substances.

It also concerns compositions in which the pharmaceutical vehicle is suitable for administration orally. Administrative forms of the invention suitable for administration orally may advantageously be gastro-resistant gelules, compressed tablets, tablets, pills, or also presented in the form of liposomes.

Other pharmaceutical compositions comprise these oligosaccharides in association with excipients suitable for administration orally. The corresponding administrative forms are constituted by suppositories.

Other forms of administration of the invention are constituted by aerosols or pommades.

The invention relates also to sterile or sterilisable injectable pharmaceutical compositions for administration both intravenously and intramuscularly or sub-contaneously.

These solutions contain advantageously 1000 to 10 000 u (Yin-Wessler)/ml of MPS, preferably from 5000 to 50 000, for example from 25 000 u/ml, when these solutions are meant for injection sub-contaneously. They may contain, for example, from 500 to 10 000, particularly 5000 u/ml of MPS when they are intended for injection intravenously or by perfusion.

Advantageously, such pharmaceutical preparations are presented in the form of discardable ready-foruse syringes.

The invention relates also to pharmaceutical compositions containing the above-defined MPS compositions in association with another active substance, useful in particular for the prophylaxis and the treatment of thrombosis, such as a venotonic agent like dihydroergotamine, an nicotinic acid salt or a thrombolytic agent like urokinase.

These pharmaceutical compositions of the invention are particularly adapted for the control (preventive or curative) of certain steps of blood clotting in men or animals, particularly in the case when the patient is subject to hypercoagulability risks resulting particularly from surgical operations, from atheromatous processes, the development of tumors and disorders of clotting through bacterial or enzymatic activators, etc.

Certain compositions are more especially suited to combat aging of the tissues or manifestations of degenerative type such as alopecias.

DESCRIPTION OF PREFERRED EMBODIMENTS

Figure 2:
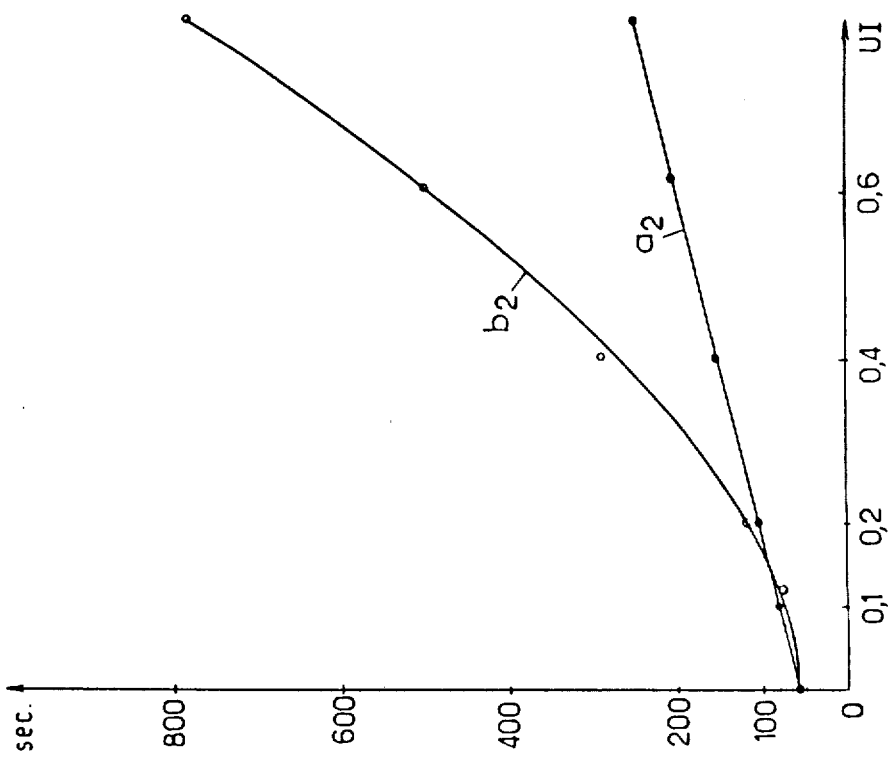

In order to illustrate the invention, there are indicated below, examples of administration to men and animals, including an example of posology usable in men: this posology comprises, for example, administration to the patient of 1000 to 25 000 u (Yin and Wessler) subcutaneously, once to three times daily, according to the level of hypercoagulability risks or the thrombotic condition of the patient, or from 1000 to 25000 u/24 hours, intraveneously, in discontinuous administrations at regular intervals, or continuously by perfusion, or again from 1000 to 25000 u (thrice weekly) intramuscularly or subcutaneously (these titers are expressed in Yin-Wessler units). These doses can naturally be adjusted for each patient according to the results and analyses of the blood carried out previously, the nature of the disorders from which they suffer and, generally, the state of health.

Besides pharmaceutical compositions containing MPS compositions as such, the invention relates also to pharmaceutical preparations containing at least one MPS composition as defined above, conjugated, by covalent linkage, to a soluble support or an insoluble support, advantageously by means of the reducing terminal sugar.

Conjugates fixed to preferred soluble supports are constituted by oligosaccharides conjugated with AT III.

Such products constitute particularly interesting medicaments in the prevention of thromboses, in the case of AT III deficiencies.

Other preferred conjugates with soluble supports are formed from an MPS composition fixed to a vehicle such as a protein, particularly polylysine, or bovine albumin serum.

These products are useful as immunogens themselves sources of circulating antibodies produced in vivo or monoclonal antibodies, cloned in vitro by to suitable techniques.

In other preferred conjugates, the compositions of the invention are conjugated to insoluble supports. Advantageously conventional supports are used.

These conjugates are useful as immunoabsorbents, for example for a purification of high specificity of AT III and for its measurement or development by fixation to biocompatible polymers, or novel athrombotic hemocompatible polymers.

The invention relates also to the use of the compositions concerned in nuclear medicine, as radiopharmaceutical products. These products are then marked by tracers selected from among those currently used in this field, and particularly by means of technetium 99 m.

To this end, technetium 99 m obtained from commercial generators, in the form of non-reactive valence 7 sodium pertechnetate, is converted into technetium reduced to valence 4 which would be the most reactive form of technetium. This conversion is carried out by means of a reducing system effected from tin salts (stannous chloride), iron salts (ferrous sulfate), titanium salts (titanium trichloride) or other salts.

Most of the time, this simple reduction of the technetium suffices, under given pH conditions, to effect the fixation of the technetium to the molecule concerned.

It is possible to use the products of the invention, which constitute in a way a support, at doses of the order of 100 to 200 u Yin-Wessler.

For developing these radiopharmaceutical reagents, it is possible to operate according to the method of P. V. KULKARNI et al. in the Journal of Nuclear Medecine 21, N° 2, p. 117-121.

The products thus marked are advantageously used in in vivo tests for the detection and extension diagnosis of thromboses and thrombotic states.

The invention relates equally also to the use of the mucopolysaccharides according to the invention to the constitution of biological reagents useful in the laboratory, particularly as a comparison reference for the study of other products of which the anticoagulant activity is tested, particularly at the level of inhibition of the Xa factor.

Other characteristics and advantages of the invention will appear in the examples which follow Examples 1 and 2 relate to the preparation of MPS compositions possessing a ratio of the YW to USP titers of the order of 4.

EXAMPLE 1

500 g of injectable heparin, in the form of sodium salt, are placed in solution in 4500 ml of demineralized water, at a temperature of 18° C.

The YW/USP ratio of the neparin used is in the vicinity of 1, these titers having a value of the order of 160–170.

The solution obtained is subjected to vigorous stirring, and its pH is lowered to 2.5 by the addition of concentrated hydrochloric acid. Then 15 g of sodium nitrite dissolved in 300 ml of water are added. The pH of the reaction is adjusted to 2.5 by concentrated hydrochloric acid, and the total value of the solution is brought to 5000 ml. The reaction is left to take place for 45 minutes and then the absence of residual nitrous ions in the reaction solution is checked, by means of indicator paper impregnated with starch potassium iodide (development of a blue-violet colour in the presence of $NO_2^-$ ions).

The reaction is allowed to continue up to the total disappearance of nitrous ions and the absence of reaction with iodo-starch paper, by carrying out checks every 3 or 4 minutes.

When these checks become negative, the reaction is considered as having been completed.

The pH of the solution is then raised to 10 by means of concentrated soda, and 5 g of sodium tetrahydroborate is added.

The solution is kept under stirring for 15 hours.

The unreacted sodium tetrahydrideborate is destroyed by lowering the pH to 3 by means of concentrated hydrochloric acid. The solution is subjected to stirring for 15 minutes, then the pH is readjusted to 7.0 by means of concentrated soda.

The reaction products are recovered by the addition of 10 l of ethanol. After 48 hours standing, the product is decanted and the supernatant liquor removed.

The precipitate is redissolved in 9 liters of demineralized water. 100 g of sodium chloride are added, and the pH of the solution is lowered to 3.8 by means of concentrated hydrochloric acid. The volume is adjusted exactly to 10 liters by means of demineralized water, and with vigorous stirring 10 liters of ethanol are added. This is left to stand 48 hours. The supernatant liquor is siphoned off and put aside. The precipitate is recovered, washed with ethanol, ground, dried under vacuum.

230 grams of product having the following characteristics are obtained:

USP titer=52 uI/mg
Yin and Wessler titer=225 uI/mg
Average molecular weight=4000 to 5000 daltons

EXAMPLE 2

5000 g of injectable heparin are dissolved in 45 liters of demineralized water, at 18° C.

In similar manner to example 1 the procedure is followed multiplying the amounts of reagents by 10, that is to say:

by adding 150 g of sodium nitrite in solution in three liters of water.
by adjusting the volume of the reaction to 50 liters.
by adding 50 g of tetrahydroborate.
by precipitating by means of 100 liters of ethanol.
by redissolving 90 l of water.
by adding 1000 g of sodium chloride.
by adjusting the final volume to 100 liters.
by finally adding 100 liters of ethanol.

In this way 2230 g of product are obtained having the following characteristics:
USP titer=54 uI/mg
Yin and Wessler titer=232 uI/mg
Average molecular weight=4000 to 5000 daltons.

The products of the reaction are recovered by addition of 10 l of ethanol, left to stand 48 hours, decanted and the supernatant liquor removed.

The precipitate is redissolved in 9 liters of demineralized water, 100 g of sodium chloride are added, and the pH of the solution is lowered to 3.8 by means of concentrated hydrochloric acid. The volume is adjusted exactly to 10 liters by means of dimineralized water, and with vigorous stirring 10 liters of ethanol are added. It is left to stand 48 hours. The supernatant liquor is syphoned of and put aside: the precipitate is recovered, washed with ethanol, ground, dried under vacuum.

230 grams of product having the following characteristics are obtained:
USP titer=52 uI/mg
Yin and Wessler titer=225 uI/mg
Average molecular weight=4000 to 5000 daltons.

In example 3 given below, the results of pharmacological tests carried out with the product of example 1, are reported.

EXAMPLE 3

On FIGS. 1 to 4 are reported the curves obtained by studying, in vitro, the variation of the clotting times induced in human blood plasmas by increasing doses of commercial heparin and the product of example 1.

In the tests corresponding to the results given in FIGS. 3 and 4, plasmas free of platelets were used, that is to say impoverished in factor XI.

These figures show the variations on thrombin time in seconds (FIG. 1), of cephalin-kaolin (FIG. 2), of coagulation in presence of concentrated thromboplastin (FIG. 3) and of dilute thromboplastin (FIG. 4), induced by the tested products, namely, the product of example 1 (curves a1, a2, a3 and a4) and of heparin (curves b1, b2, b3, b4) according to the doses respectively used.

Figure 1:
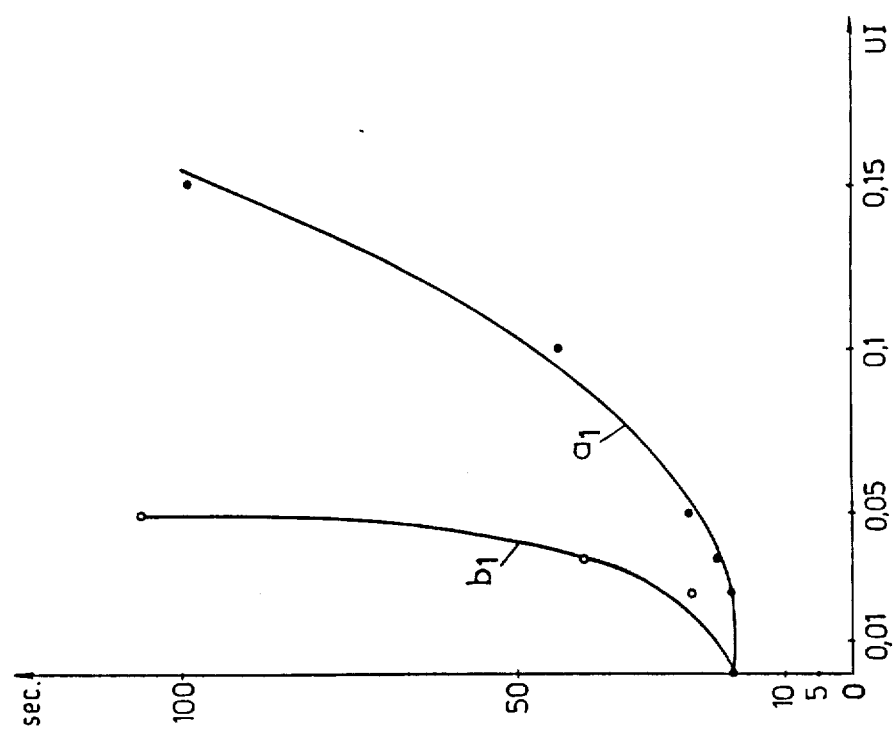

The thrombin times and the cephalin-kaolin times both constitute types of measurement reflecting rather the action of the preparation studied respectively on the inhibition of the activated factor II and the overall coagulation. Study of the curves of FIGS. 1 and 2 shows that the MPS according to the invention exert a distinctly smaller effect than that of heparin on the inhibition of activation of prothrombin and at the level of the overall coagulation. FIGS. 3 and 4 which are representative of phenomena more directly connected with the sequence of enzymatic reactions, characteristics of extrinsic coagulation (particularly in the relative absence of factor IIa), show the advantageous effect of the MPS of the invention with respect to heparin.

The example 4 below concerns the results of tests in vivo in the rabbit with the MPS of example 2.

EXAMPLE 4

Study of the antithrombotic activity of the product of example 2 in the rabbit.

The administration of 500 u YW to the rabbit causes a considerable anti-Xa activity whilst the overall anticoagulant activity remains relatively low.

Two hours after the administration, the YW activity is of the order of 0.88 u/ml whilst the cephalin kaolin time is 0.09 ui.ml.

The in vitro and in vivo tests show therefore the distinctly more selective action of the MPS of the invention, particularly at the level of inhibition of the Xa factor, than that of heparin.

We claim:

1. A process for the preparation of mucopolysaccharides having higher antithrombic activity and a lower ratio of YW/USP and lower YW titer than the starting mucopolysaccharides, which process comprises treating mucopolysaccharide fractions, having a high antithrombic activity and a ratio of YW/USP titers higher than that of heparin and having mucopolysaccharide chains which contain less than about 6 units with an acidic aqueous mixture which contains an inorganic salt and an organic solvent in which solvent the inorganic salt is miscible and in which aqueous mixture mucopolysaccharides which have chains of 6 units and greater are insoluble and recovering mucopolysaccharides free of mucopolysaccharide chains of less than 6 units, thereby having performed a fractionation of the starting mucopolysaccharides having an average higher molecular weight.

2. The process of claim 1 wherein the mucopolysaccharides have a 2,5-anhydromanno-terminal structure at the reducing end.

3. The process of claim 2 wherein the 2,5-anhydromannose structure is selected from the group consisting of 2,5-anhydromannose, 2,5-anhydromannitol and 2,5-anhydromannonic acid.

4. The process of claim 1 wherein the organic solvent is an alcoholic solvent.

5. The process of claim 4 wherein the alcoholic solvent is ethanol.

6. The process of claim 1 wherein the inorganic salt is a salt miscible in the organic solvent.

7. The process of claim 1 wherein the inorganic salt is selected from the group consisting of sodium chloride and potassium chloride.

8. The process of claim 1 wherein the aqueous mixture is acidic to below a pH of 4.

9. The process of claim 8 which comprises dissolving the starting mucopolysaccharides in water, adding the inorganic salt, lowering the pH to an acidic pH and adding the organic solvent to said aqueous mixture.

10. The process of claim 9 wherein there is dissolved about 5% per weight of mucopolysaccharides in water containing 10 g/l of ethanol, adjusting the pH to about 3.8 and recovering the precipitate.

11. The process of claim 1 wherein the starting mucopolysaccharides have a ratio of YW to USP titers of at least about 10 and a YW titer of about 200 to 250 u/mg.

12. The process of claim 1 wherein the organic solvent causes the precipitation of the mucopolysaccharides which have a ratio of YW to USP titers less than 6.

13. The process of claim 9 wherein after the addition of the organic solvent, a precipitate is formed, which is recovered.

14. The process of claim 13 wherein the inorganic salt is sodium chloride and the organic solvent is ethanol.

15. The process of claim 13 which comprises washing the recovered precipitate.

16. A process for the preparation of mucopolysaccharides having YW and USP titers in a ratio of about 6 to 3, and a YW titer higher than that of heparin, of at least 180–200 u, comprises using an heparin aqueous solution, said heparin having a YW/YSP ratio of about 1, the YW and USP titers being respectively of about 160–170, lowering the pH to 2.5, adding an aqueous solution of sodium nitrite, sodium nitrite being used in an amount of 15 g dissolved in 300 ml of water when using a solution of heparin containing 500 g of heparin, in the form of sodium salt, in solution in 4500 ml of water, adjusting the pH to 2.5, ajusting the reaction volume, the total volume being brought to 5000 ml when using said concentrations of reactants, allowing the reaction to take place up to the total disappearance of nitrous acid, raising to 10 the pH of the solution, adding tetrahydroborate, eliminating the unreacted sodium tetrahydroborate and adjusting the pH to 7.0, adding 10 l of ethanol and recovering the insoluble products, redissolving the precipitate in 9 l of water, adding sodium chloride in a proportion of 100 g in view of the above concentration, lowering the pH to 3.8, adjusting the final volume to 10 liters, adding 10 liters of ethanol, precipitating a solid and recovering the solid.

17. The process of claim 11 wherein the ratio of YW to USP is about 4.

* * * * *

UNITED STATES PATENT AND TRADEMARK OFFICE
CERTIFICATE OF CORRECTION

PATENT NO. : 4,686,288
DATED : Aug. 11, 1987
INVENTOR(S) : Jean-Claude Lormeau et al It is certified that error appears in the above-identified patent and that said Letters Patent are hereby corrected as shown below:

Col. 6, lines 48-61    Delete entire section beginning "The precipitate ..." through "4000 to 5000 daltons."

Col. 7, line 47    Insert after "YW/USP" the word --titers--

Signed and Sealed this

Fourteenth Day of June, 1988

*Attest:*

DONALD J. QUIGG

*Attesting Officer*    *Commissioner of Patents and Trademarks*